United States Patent
Chen

(10) Patent No.: US 10,267,713 B2
(45) Date of Patent: Apr. 23, 2019

(54) SAMPLE PREPARATION SYSTEM AND PREPARATION METHOD FOR AN ELECTRON MICROSCOPE

(71) Applicant: Materials Analysis Technology Inc., Hsinchu (TW)

(72) Inventor: Hung-Jen Chen, Hsinchu (TW)

(73) Assignee: Materials Analysis Technology Inc., Hsinchu County (TW)

( * ) Notice: Subject to any disclaimer, the term of this patent is extended or adjusted under 35 U.S.C. 154(b) by 176 days.

(21) Appl. No.: 15/372,396

(22) Filed: Dec. 8, 2016

(65) Prior Publication Data

US 2018/0095015 A1    Apr. 5, 2018

(30) Foreign Application Priority Data

Oct. 5, 2016 (TW) .............................. 105132189 A

(51) Int. Cl.
| | |
|---|---|
| G01N 1/00 | (2006.01) |
| G01N 1/28 | (2006.01) |
| H01J 37/20 | (2006.01) |
| H01J 37/26 | (2006.01) |
| G01N 1/06 | (2006.01) |

(52) U.S. Cl.
CPC ............... *G01N 1/286* (2013.01); *G01N 1/06* (2013.01); *H01J 37/20* (2013.01); *H01J 37/26* (2013.01); *G01N 2001/2873* (2013.01); *H01J 2237/204* (2013.01); *H01J 2237/2007* (2013.01)

(58) Field of Classification Search
CPC .. G01N 1/286; G01N 1/06; G01N 2001/2873; H01J 37/20; H01J 37/26; H01J 2237/2007; H01J 2237/204
See application file for complete search history.

(56) References Cited

U.S. PATENT DOCUMENTS

| | | | | |
|---|---|---|---|---|
| 8,635,934 B2 * | 1/2014 | Kong | ....................... | G01N 1/06 83/167 |
| 2015/0050650 A1 * | 2/2015 | Seppo | .................. | C12Q 1/6841 435/6.11 |
| 2015/0300924 A1 * | 10/2015 | Miyatani | .................. | G01N 1/06 83/98 |

FOREIGN PATENT DOCUMENTS

| | | |
|---|---|---|
| CN | 102414549 | 7/2013 |
| CN | 104520689 | 4/2015 |

(Continued)

OTHER PUBLICATIONS

"Office Action of Taiwan Counterpart Application," dated May 19, 2017, p. 1-p. 5, in which the listed references were cited.

*Primary Examiner* — Harshad R Patel
*Assistant Examiner* — Nigel H Plumb
(74) *Attorney, Agent, or Firm* — JCIPRNET

(57) ABSTRACT

A sample preparation system includes a slicing module, a first tank, a sequencing module and a pickup module. The slicing module is utilized to sequentially slice a sample block into a plurality of sample slices. The first tank is utilized to receive the sample slices. The sample slices float on a fluid in the first tank, and the sample slices are moved by the flowing fluid. The sequencing module is disposed at a side of the first tank, so as to separate the sample slices sequentially. The pick module is coupled with the first tank, so as to pick up the sample slices sequentially and place the sample slices on corresponding sample holders. In addition, a sample preparation method is also provided.

16 Claims, 15 Drawing Sheets

(56) References Cited

FOREIGN PATENT DOCUMENTS

| | | |
|---|---|---|
| CN | 104755903 | 7/2015 |
| CN | 104977199 | 10/2015 |

\* cited by examiner

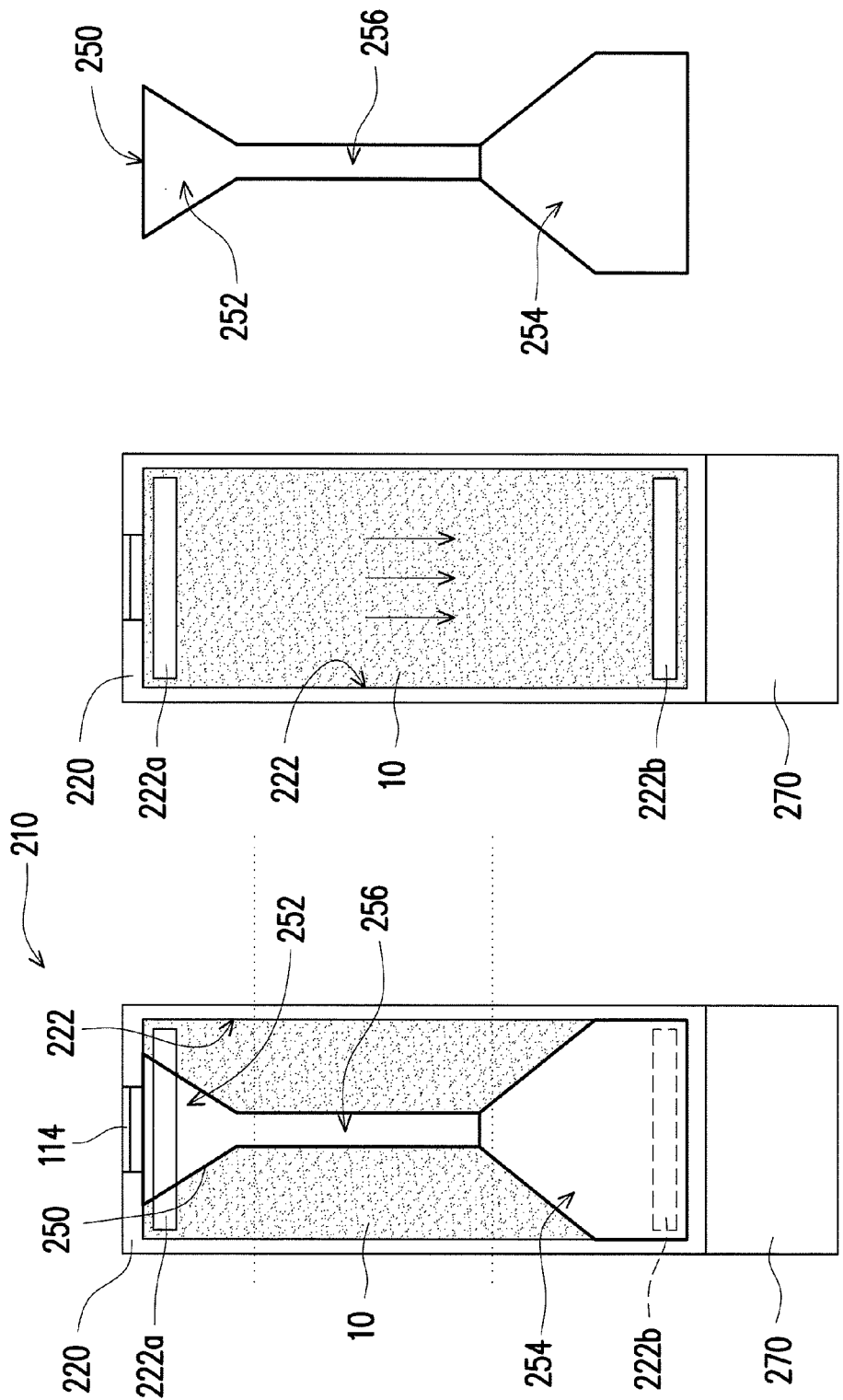

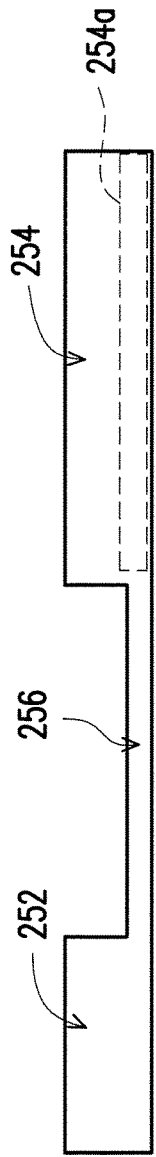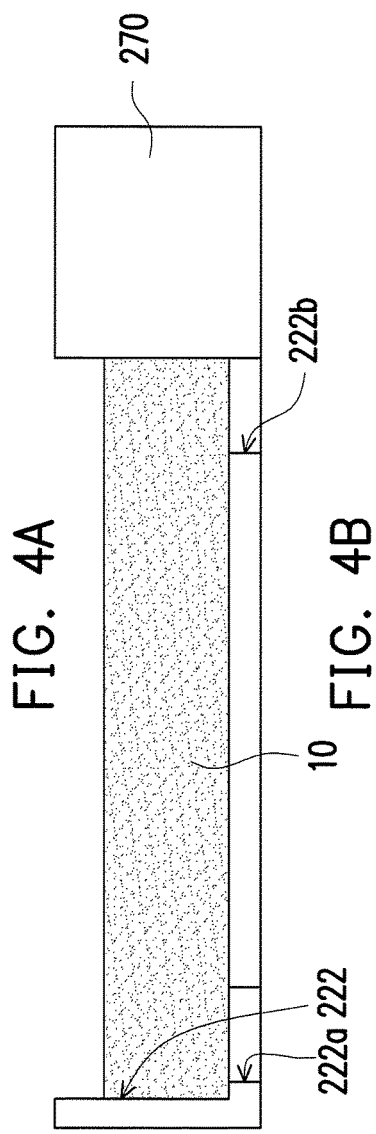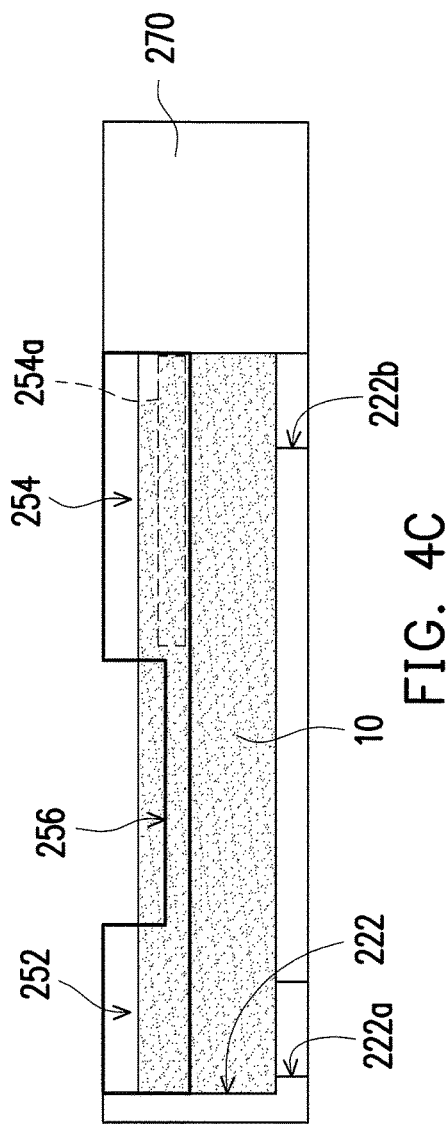

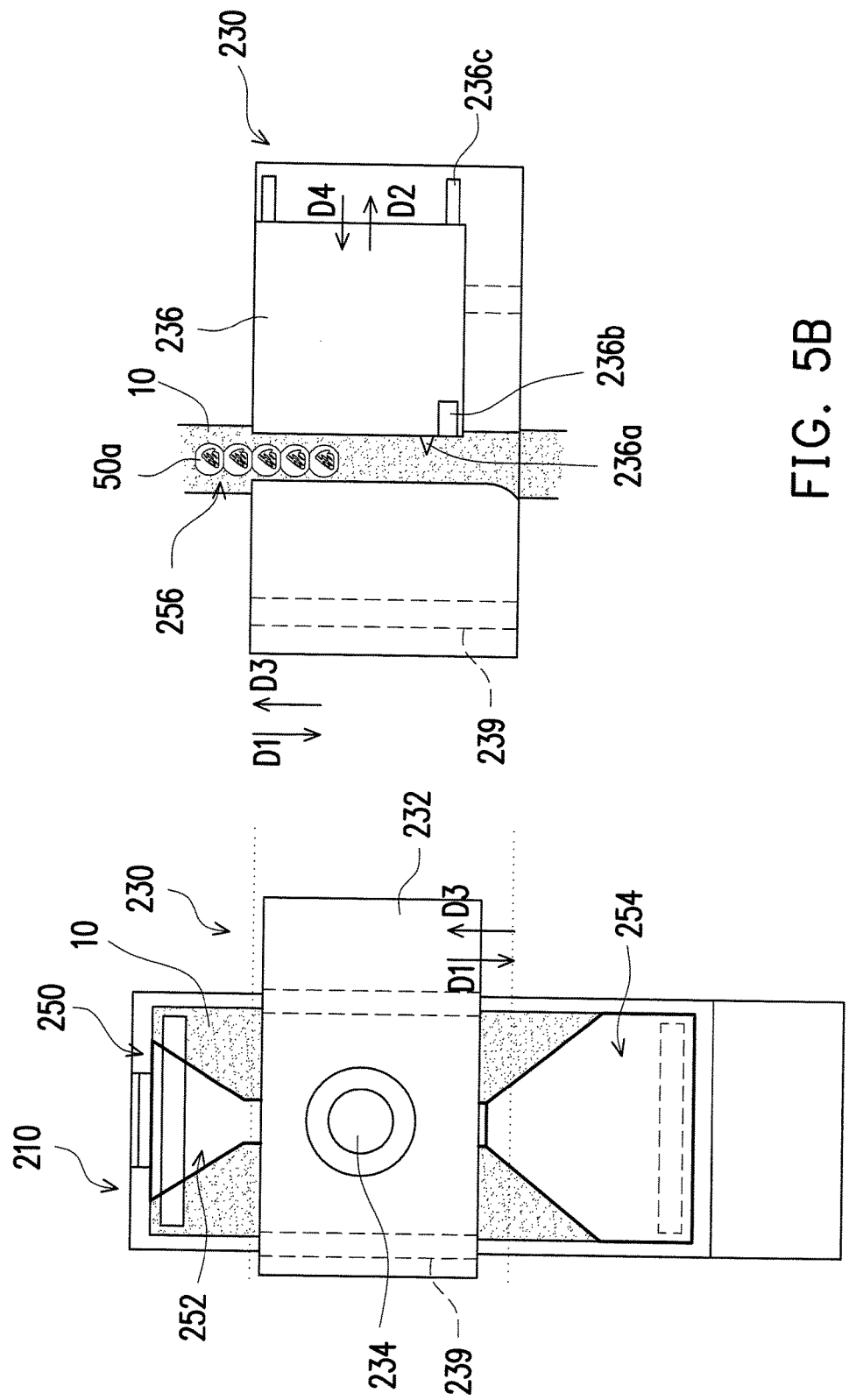

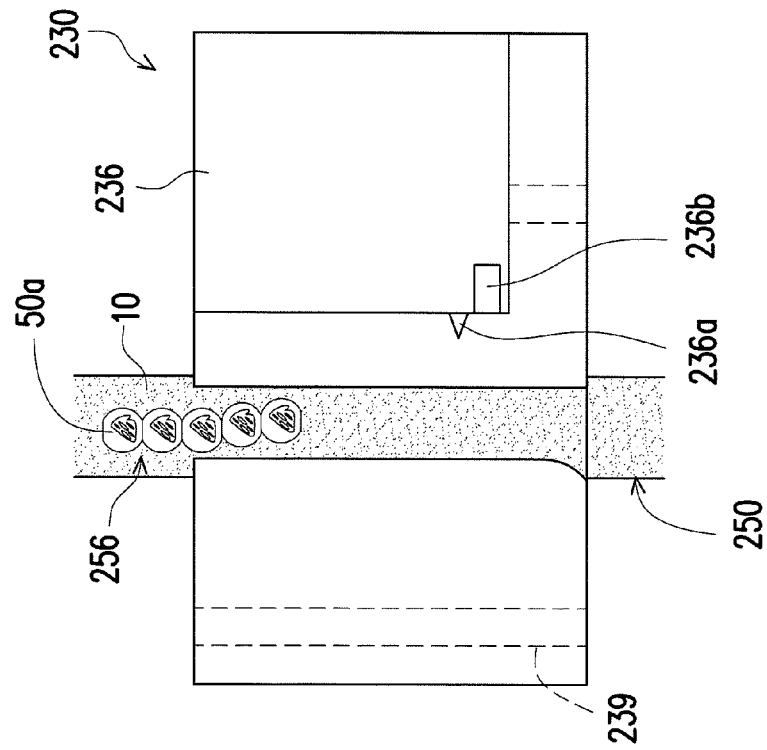
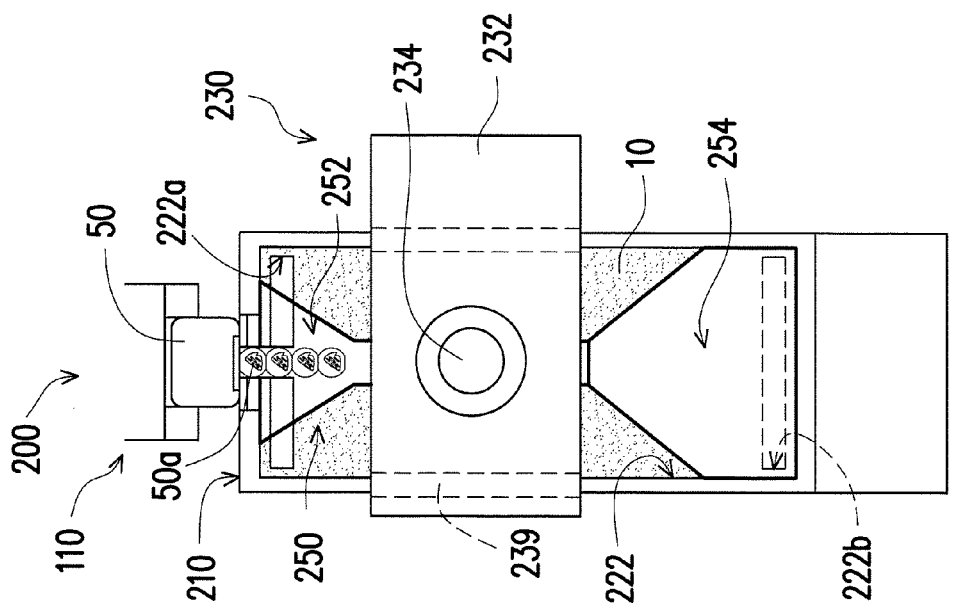
FIG. 6B
FIG. 6A

SAMPLE PREPARATION SYSTEM AND PREPARATION METHOD FOR AN ELECTRON MICROSCOPE

CROSS-REFERENCE TO RELATED APPLICATION

This application claims the priority benefit of Taiwan application serial no. 105132189, filed on Oct. 5, 2016. The entirety of the above-mentioned patent application is hereby incorporated by reference herein and made a part of this specification.

BACKGROUND

1. Field of the Invention

The present disclosure generally relates to a sample preparation system and a preparation method of an electron microscope, and more particularly, to a sample preparation system and a preparation method capable of sequentially and automatically preparing samples.

2. Description of Related Art

By applying a high-resolution three-dimensional (3D) imaging technology of an electron microscope in applications of clinical medical and biomolecular research, resolution of observation images and accuracy of observation results can be effectively increased. However, during a process of establishing a high-resolution 3D image, a large number of ultra-thin samples is required to be prepared, and during an observation process of the samples, a precise positioning of the image is required. In current preparation processes for a sample block of the electron microscope, mostly still require to manually embed the samples in a resin one-by-one using embedding capsules. Therefore, when it is in need to observe a large number of samples, a lot of manpower and time costs are spent on the preparation of the samples. In addition, production qualities of the individually prepared samples are varied and thus cause the qualities of the samples being observed to be inconsistent, thereby influencing observation qualities of the samples. Accordingly, how to effectively increase the production efficiency and qualities of the sample slices of the electron microscope and improve the current sample preparation system has become an important issue in the development of the current electron microscope observation technology.

SUMMARY

The present disclosure provides a sample preparation system capable of sequentially slicing an electron microscopic sample into a plurality of sample slices, wherein the sample slices can be arranged and sequenced by a sequencing module and a pickup module.

The present disclosure provides a sample preparation method capable of completing preparations and sequential arrangements of a plurality of electron microscopic samples at the same time.

The sample preparation system of the present disclosure includes a slicing module, a first tank, a sequencing module and a pickup module. The slicing module is configured to sequentially slice a sample block into a plurality of sample slices. The first tank is configured to receive the sample slices, and the sample slices are adapted to float on a fluid in the first tank and be moved as the fluid flows. The sequencing module is disposed at a side of the first tank so as to separate the sample slices sequentially. The pickup module is coupled to the first tank so as to pick up the sample slices sequentially from the first tank and place the sample slices on corresponding sample holders.

The sample preparation method of the present disclosure includes: sequentially slicing a sample block into a plurality of sample slices by a slicing module; receiving the sample slices with a first tank, wherein the sample slices float on a fluid in the first tank; enabling the sample slices to flow with the fluid to a separation position in the first tank; sequentially separating the sample slices at the separation position by a sequencing module; and picking up the separated sample slices from the first tank by a pickup module, and sequentially placing and arranging the sample slices on a sample holder.

In one embodiment of the present disclosure, the slicing module includes a clamping portion and a cutting tool. The clamping portion is configured to clamp the sample block, and the cutting tool is disposed at an edge of the first tank so as to sequentially slice the sample block.

In one embodiment of the present disclosure, the first tank includes a tank body, a receiving area and a pickup area. The tank body has a chamber and a liquid inlet and a liquid outlet connected through with the chamber. The fluid enters the chamber via the liquid inlet, and leaves the chamber from the liquid outlet by flowing along a flow channel. The flow channel includes a receiving area, a pickup area and a sequencing area. The receiving area is adjacent to the liquid inlet and configured to receive the sample slices. The pickup area is adjacent to the liquid outlet, and the pickup module picks up the sample slices from the pickup area. The sequencing area is located between the receiving area and the pickup area, the sample slices sequentially pass through the sequencing area, and the sequencing module separate the sample slices.

In one embodiment of the present disclosure, a width of the sequencing area is smaller than widths of the receiving area and the pickup area.

In one embodiment of the present disclosure, the sequencing module is disposed on the flow channel, and the sequencing module includes a first body, a first detection device and a separation device. The first detection device is disposed corresponding to the flow channel so as to determine positions of the sample slices. The separation device is disposed on the first body and adapted to move towards the sample slices in the first tank so as to separate two adjacent sample slices.

In one embodiment of the present disclosure, the sequencing module further includes a piezoelectric device coupled to the separation device. The piezoelectric device is configured to drive the separation device into vibration so as to separate the two adjacent sample slices.

In one embodiment of the present disclosure, the first body of the sequencing module is slidably disposed on the first tank along a first direction.

In one embodiment of the present disclosure, the separation device of the sequencing module is slidably disposed on the first body along a second direction, and the first direction and the second direction are orthogonally intersected.

In one embodiment of the present disclosure, the pickup module includes a second body, a pickup device and a second detection device. The pickup device is disposed on the second body. The second detection device is disposed corresponding to the first tank so as to detect positions of the sample slices. The pickup device is adapted to move relative to the first tank according to a detection result of the second positioning unit, so as to pick up the sample slices sequentially from the pickup area and to place the sample slices on the corresponding sample holders.

In one embodiment of the present disclosure, the sample preparation system further includes a second tank coupled to a side of the first tank or disposed in the first tank. The second tank is adapted to receive the sample slices from the slicing module, and the sample slices are carried by the fluid to move from the second tank to the first tank.

In one embodiment of the present disclosure, profile shapes of the sample slices comprise trapezoids, double truncated circles or polygons.

In one embodiment of the present disclosure, the sample preparation method further includes: when the slicing module sequentially slices the sample block, with a profile shape design of the sample block, enabling the sequentially sliced sample slices received by the first tank to lap over each other to form a sample chain floating on the fluid in the first tank.

In one embodiment of the present disclosure, the sequencing module has a separation device configured to approach or contact the sample chain and to separate each of the sample slices.

In one embodiment of the present disclosure, the sample preparation method further includes: after the slicing module sequentially slices the sample block into the sample slices, receiving the sample slices from the slicing module with a second tank.

In one embodiment of the present disclosure, the sample preparation method further includes: s transferring the sample slices from the second tank to the first tank. The second tank is movably embedded at a side of the first tank or disposed in the first tank. The fluid s injected into the second tank to carry the sample slices from the second tank to the first tank with the fluid, so as to sequentially perform subsequent separation steps of the sample slices.

In view of the above, the sample preparation system and the sample preparation method in the embodiments of the present disclosure can complete the sequential slicing of the sample block via the slicing module and the transferring of the sample slices with the fluid in the tanks. In addition, the sequencing module can sequentially separate the sample slices that pass through the flow channel and then transfer the sample slices onto the sample holders via the pickup module, so as to sequentially arrange the sample slices in order. In the embodiments of the present disclosure, the sample block can be sliced into a plurality of sample blocks having a same profile or a continuous trend of profile variation. Therefore, the profile of the sample block can be used to observe the order and the arrangement of the different sample slices. In addition, in the embodiments of the present disclosure, the sample preparation system can achieve a sequential preparation of a large number of thin sample slices in an automated manner, and thereby reduces the manpower and the production costs being required.

In order to make the aforementioned features and advantages of the disclosure more comprehensible, embodiments accompanying figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

FIG. 3A to FIG. 3C are schematic top views illustrating partial components of the sample preparation system of FIG. 2.

FIG. 4A to FIG. 4C are schematic side views illustrating partial components of the sample preparation system of FIG. 2.

FIG. 5A to FIG. 5B are schematic views illustrating a sequencing module in the sample preparation system of FIG. 2.

FIG. 6A to FIG. 6H are schematic views illustrating an actuation means of the sequencing module in the sample preparation system of FIG. 2.

DESCRIPTION OF THE EMBODIMENTS

Figure 1B:
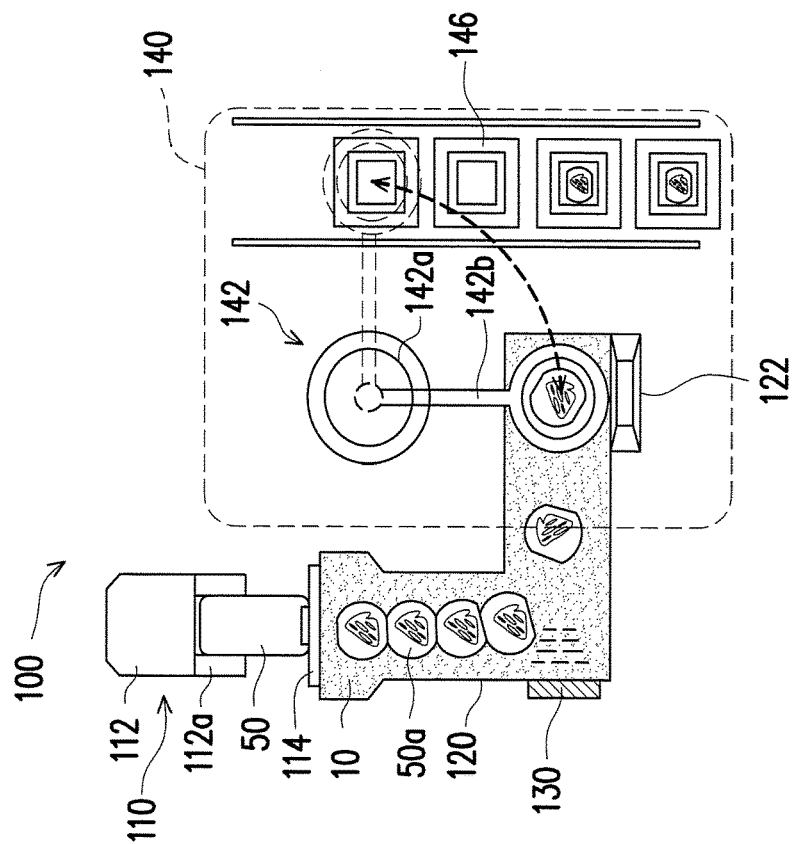
FIG. 1A and FIG. 1B are schematic views illustrating a sample preparation system according to an embodiment of the present disclosure.
Figure 1A:
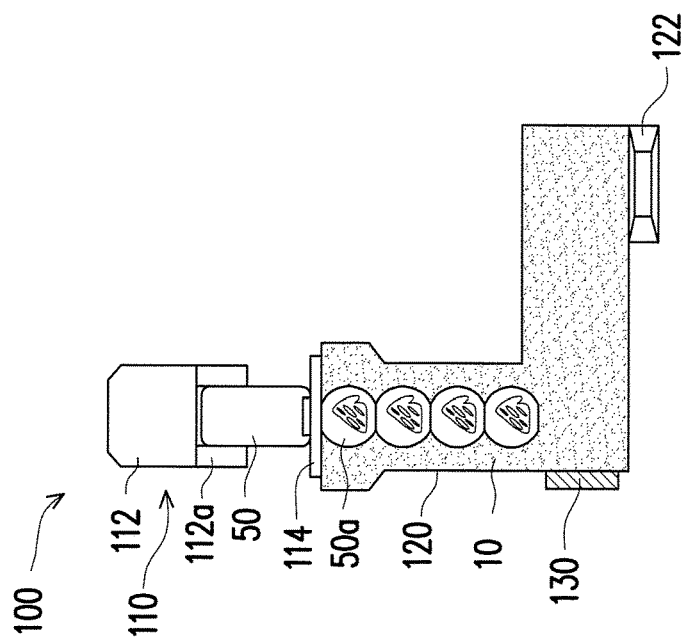

FIG. 1A and FIG. 1B are schematic views illustrating a sample preparation system 100 according to an embodiment of the present disclosure. Referring to FIG. 1A and FIG. 1B, the sample preparation system 100 includes a slicing module 110, a first tank 120, a sequencing module 130 and a pickup module 140. The slicing module 110 can be utilized to sequentially slice a sample block 50 into a plurality of sample slices 50a. For instance, a sample desired to be observed under an electron microscope can be firstly buried in a resin block to form the sample block 50. After the sample block 50 is sliced by the slicing module 110, a plurality of sample slices 50a having a continuous profile can be formed, and the sample slices 50a may include sample slices in the middle and resin parts surrounding the sample slices.

The first tank 120 can be utilized to receive the sample slices 50a. The sample slices 50a can float on a fluid 10 in the first tank 120 and be moved as the fluid 10 flows. Therefore, the sample slices 50a are respectively carried by the fluid 10 to sequentially move from the slicing module 110 to the sequencing module 130 shown in FIG. 1A.

As shown in FIG. 1A, the sequencing module 130 can be disposed at a side of the first tank 120, and the sequencing module 130 can sequentially separate the sample slices 50a sliced by the slicing module 110. In addition, as shown in FIG. 1B, the pickup module 140 can be coupled to the first tank 120, and the pickup module 140 can sequentially move the sample slices 50a from the first tank 120 onto corresponding sample holders 146 by means of, for example, mechanical arm clamping.

In the present embodiment, the slicing module 110 includes a clamping portion 112 and a cutting tool 114. The clamping portion 112 can be utilized to camp the sample block 50, and the clamping is, for example, performed by means of using a flexible clamping arm 112a. Further, the cutting tool 114 is disposed at an edge of the first tank 120 so as to sequentially slice the sample block 50. In the present embodiment, the cutting tool 114 is, for example, a diamond knife or a glass knife.

In the present embodiment, the first tank 120 has a counterbore hole 122, and a flow volume or a flow rate of the fluid 10 in the first tank 120 can be controlled by changing a configurational height or a design size of the counterbore hole 122. In addition, the sequencing module 130 is, for example, a piezoelectric module which can be triggered to produce vibration so as to separate the sample slices 50a sequentially entering the first tank 120.

Specifically, in the present embodiment, a method of initiating the fluid 10 in the first tank 120 to flow includes, for example, driving the fluid 10 to flow by using a pump, adjusting an included angle of the first tank 120, using mechanical components to enable the first tank 120 to produce vibration or movement, natural convection of the fluid 10 or so forth.

Referring to FIG. 1B, in the present embodiment, the pickup module 140 includes a sample pickup device 142 and a sample holder 146. For instance, the sample pickup device 142 has a fixing base 142a and a bearing arm 142b. The bearing arm 142b can carry the sample slices 50a and rotate relative to the fixing base 142a so as to take out the sample slices 50a from the first tank 120 and place the sample slices 50a sequentially on the sample holders 146.

Figure 2:
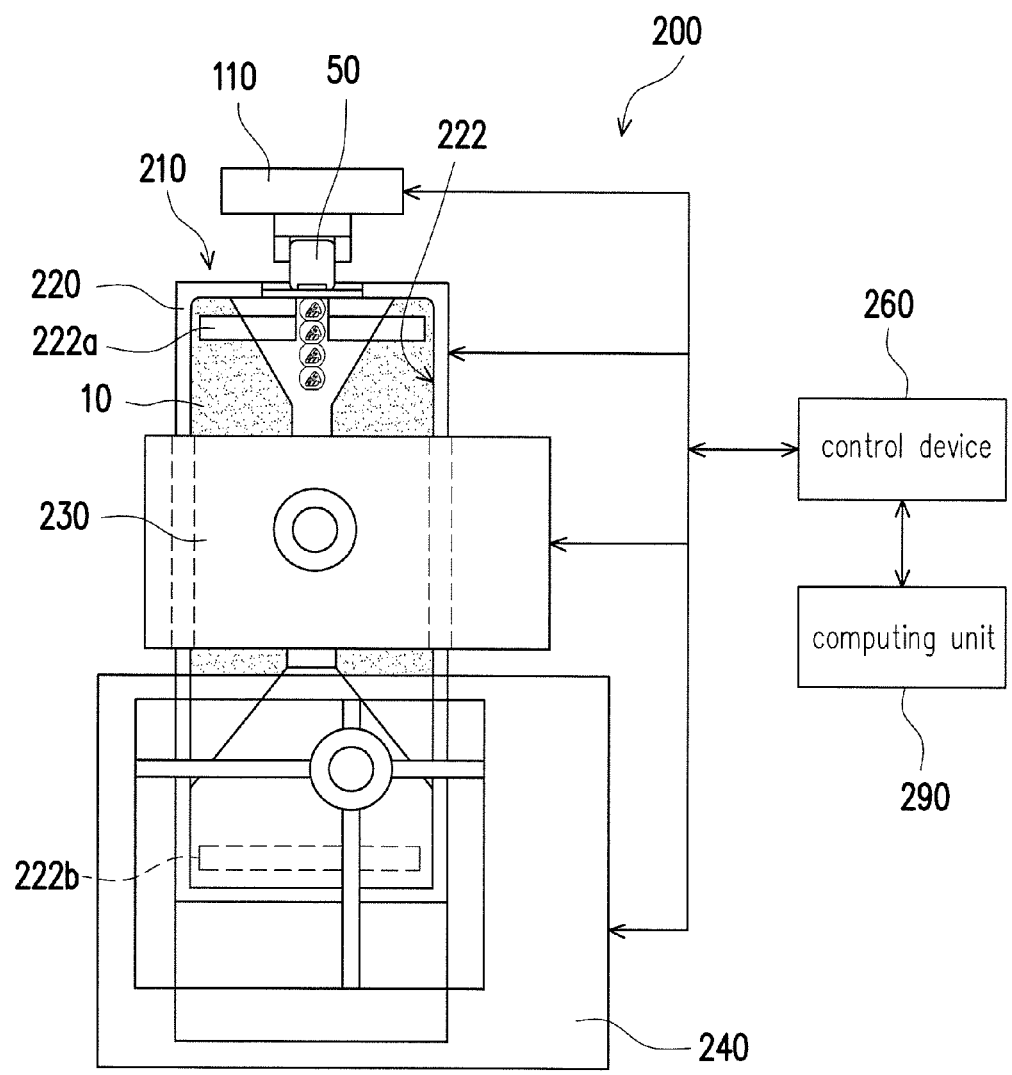
FIG. 2 is a schematic view illustrating a sample preparation system according to another embodiment of the present disclosure.

FIG. 2 is a schematic view illustrating a sample preparation system 200 according to another embodiment of the present disclosure. FIG. 3A to FIG. 3C are schematic top views illustrating partial components of the sample preparation system 200 of FIG. 2. FIG. 4A to FIG. 4C are schematic side views illustrating partial components of the sample preparation system 200 of FIG. 2. The embodiment of FIG. 2, FIG. 3A to FIG. 3C and FIG. 4A to FIG. 4C is similar to the embodiment of FIG. 1; thus, the same or similar notations are used for representing the same or similar components, and descriptions of the same technical contents are omitted. Referring to FIG. 2 and FIG. 3A to FIG. 3C, a difference between the sample preparation system 200 and the previous embodiment lies in that: the first tank 210 of the sample preparation system 200 includes a tank body 220, which has a chamber 222 and a liquid inlet 222a and a liquid outlet 222b connected through with the chamber 222. In the present embodiment, the fluid 10 can enter the chamber 222 via the liquid inlet 222a, and the fluid 10 flows in the flow channel 250 along an arrow direction shown in FIG. 3B and then exits from the liquid outlet 222b.

As shown in FIG. 3A to FIG. 3C, the flow channel 250 is, for example, an entity flow channel formed with a spacer material, such as plastic or so forth, and the flow channel 250 can be assembled in the tank body 220 of FIG. 3B so as to transfer the sample slices 50a in the first tank 210 of FIG. 3A. The flow channel 250 can be divided into a receiving area 252, a pickup area 254 and a sequencing area 256. The receiving area 252 is adjacent to the liquid inlet 222a so as to receive the sample slices 50a that enter the first tank 210. In addition, the pickup area 254 of the sample slices 50a is adjacent to the liquid outlet 222b, and the pickup module 240 can pick up the sample slices 50a from the pickup area 254.

The sequencing area 256 is located between the receiving area 252 and the pickup area 254. Referring to FIG. 2 and FIG. 3A to FIG. 3C, the sample slices 50a can sequentially pass through the sequencing area 256, and the sequencing module 230 can separate the sample slices 50a that sequentially enter the sequencing area 256. In terms of the design of the flow channel 250, a width of the sequencing area 256 of the flow channel 250 is smaller than widths of the receiving area 252 and the pickup area 254. As shown in FIG. 3A, after the pickup area 254 of the flow channel 250 receives the sample slices 50a, with a design of gradually shrinking the receiving area 252 in the flow channel, the sample slices 254 are sequentially guided into the sequencing area 256. In addition, the width of the sequencing area 256 of the flow channel 250 of the present embodiment enables the passing of one single sample slice 50a so that the sample slices 50a can one by one pass through the sequencing area 256, sequentially.

As shown in FIG. 2, FIG. 3A and FIG. 3B, the tank body 220 can be connected with a platform 270 utilized to build the pickup module 240, wherein, as shown in FIG. 2, the pickup module 240 is built above the platform 270 to enable the pickup module 240 to pick up the sample slices 50a in the pickup area 254 of the flow channel 250.

In the present embodiment, the sequencing module 230 and the pickup module 240 can be electrically coupled to a control device 260 and a computing unit 290. The computing unit 290 can transmit a control signal to the control device 260, and the control device 260 can be utilized to control the actuations of the sequencing module 230, the pickup module 240 and the associated components so as to achieve an automated operation of the sample preparation system.

Referring to the side views of the first tank 210 in FIG. 4A to FIG. 4C, in the present embodiment, when the flow channel 250 of FIG. 4A is disposed above the tank body 220, the fluid 10 can be injected into the chamber 222 of the tank body 220 from the liquid inlet 222a under the receiving area 252, and when a liquid level of the fluid 10 entering the chamber 222 is higher than a sidewall of a portion of the flow channel 250, the fluid 10 can overflow into the flow channel 250 and the sample slices 50a in the receiving area 252 of the flow channel 250 can be moved towards a direction of the sequencing area 256 and the pickup area 254 with the flowing of the fluid 10.

In the present embodiment, the bottom of the pickup area 254 of the flow channel 250 has a bottom plate 254a for blocking the separated sample slices 50a, so as to prevent the sample slices 50a from flowing out of the liquid outlet 222b with the fluid 10. Moreover, in the present embodiment, the flow rate and the flow volume of the fluid 10 in the chamber 222 and the flow channel 50 can be adjusted by changing a size design of the liquid outlet 222b or a position of the liquid outlet 222b relative to an inclined angle of the liquid inlet 222a.

FIG. 5A to FIG. 5B are schematic views illustrating the sequencing module in the sample preparation system of FIG. 2. In the present embodiment, the sequencing module 230 may include a first body 232, a first detection device 234 and the separation device 236. The first detection device 234 can be disposed corresponding to the flow channel 250 so as to determine positions of the sample slices 50a in the first tank 210. In addition, the first body 232 can have a sliding chute 239 so that the sequencing module 230, through the sliding chute 239, can be slidably disposed on a tank wall disposed in parallel thereto along an extending direction of the first tank 210. Therefore, the sequencing module 230 can slide along the extending direction of the first tank 210, namely, a first direction D1 and a third direction D3 indicated by arrows shown in FIG. 5A.

In the present embodiment, the first detection device 234 is, for example, a charge couple device (CCD), which can detect and locate the positions the sample slices 50a. In addition, the separation device 236 and the first body 232 can be disposed with a slide rail 236c therebetween so that the separation device 236, through the slide rail 236c, can be slidably disposed on the first body 232 and slide relative to the first body 232 along a second direction D2 and a fourth direction D4 indicated by arrows shown in the right side of FIG. 5B. In the present embodiment, a sliding direction of the separation device 236 relative to the first body 232 (the first and third directions D1 and D3) and a sliding direction of the first body 232 relative to the first tank 210 (the second and fourth directions D2 and D4) are orthogonally intersected.

In the present embodiment, the separation device 236 has a contact portion 236a, which is capable of approaching or contact and pushing the sample slices 50a that sequentially pass through the sequencing area 256, so as to sequentially separate the sample slices 50a that are in contact with or lapped over each other. The sequencing module 230 further includes a piezoelectric device 236b disposed at a side of the separation device 236 nearby the sequencing area 256. In addition, the piezoelectric device 236b is coupled to the separation device 236, and the piezoelectric device 236b, when being triggered into vibration, can drive the contact portion 236a of the separation device 236 into vibration so as to separate two adjacent sample slices 50a that are adjacently in contact with or lapped over each other. In the present embodiment, the piezoelectric device 236b is, for example, triggered into vibration by means of optic or physical contact.

Figure 6D:
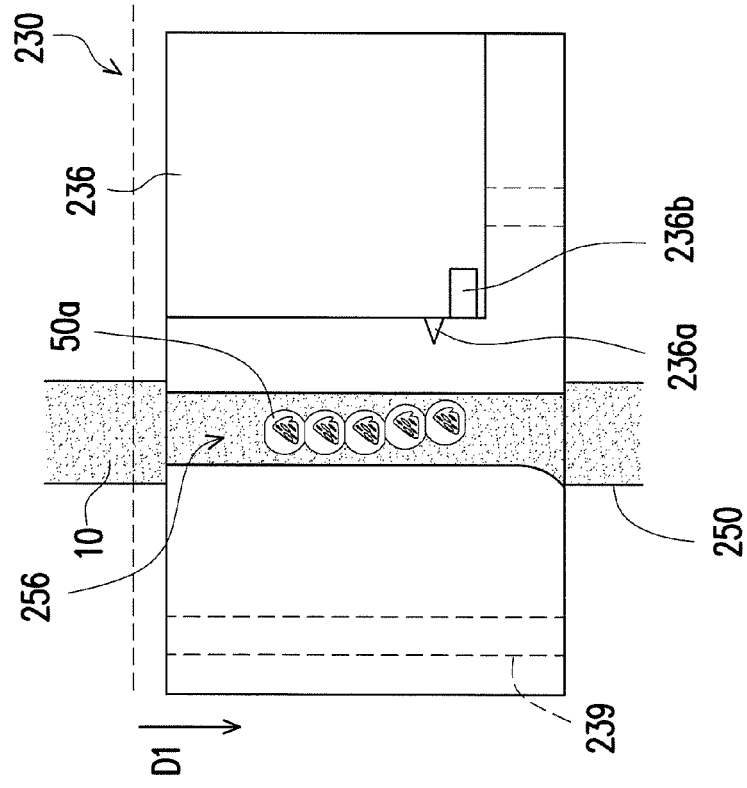

FIG. 6A to FIG. 6H are schematic views illustrating an actuation means of the sequencing module in the sample preparation system of FIG. 2. Referring to FIG. 6A and FIG. 6B, in the present embodiment, when the sample block 50 is sliced into a plurality of sample slices 50a of a same batch, the sample slices 50a are received by the receiving area of the flow channel 250 and sequentially enter the sequencing area 256 of the flow channel. At this moment, the sample preparation system 200 enables the sample slices 50a to be rested in the sequencing area 256 by adjusting the flow volume or the flow rate of the fluid 10 in the first tank 210. The first detection device 234 can detect the positions of the sample slices 50a, and the separation device 236 of the sequencing module 230 can move relative to the first body 232 according to the positions of the sample slices 50a. At the same time, the separation device 236 can be driven by the first body 232 to move along the extending direction of the first tank 210.

Noteworthily, in the present embodiment, the sample block 50, with a proper profile design, enables the sample slices 50a formed by sequentially slicing the sample block 50 to lap over each other during the process of slicing so as to form a sample chain floating on the fluid 10 of the first tank 210. In addition, the sample chain can move into the sequencing area 256 along the flow channel 250.

Figure 6C:
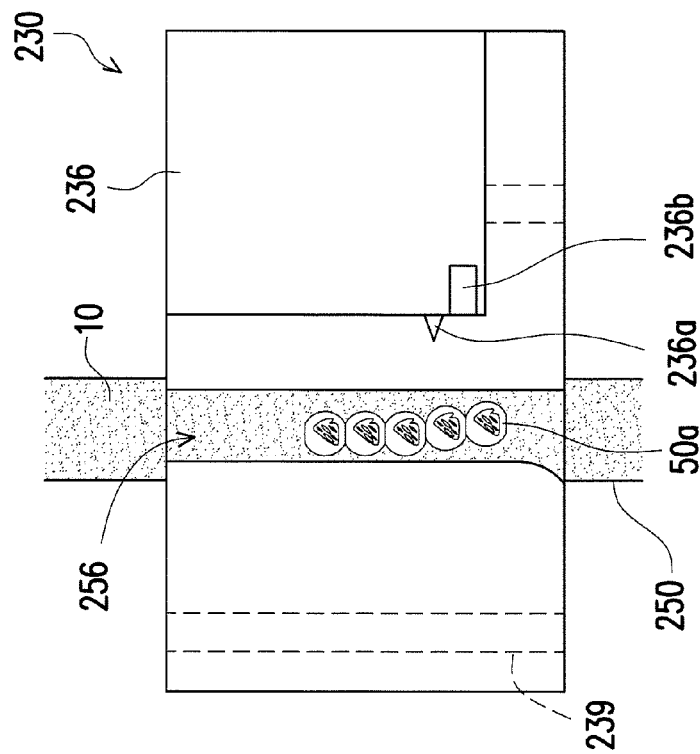

For instance, as shown in FIG. 6C and FIG. 6D, when the fluid 10 stops to flow while the sample slices 50a are rested in the sequencing area 256 and do not move with the fluid 10, the separation device 236 can move close to a position of the sample chain formed by lapping over the sample slices 50a, along a first direction D1 indicated by an arrow shown in FIG. 6D, as the first body 232 slides relative to the first tank 250.

Figure 6E:
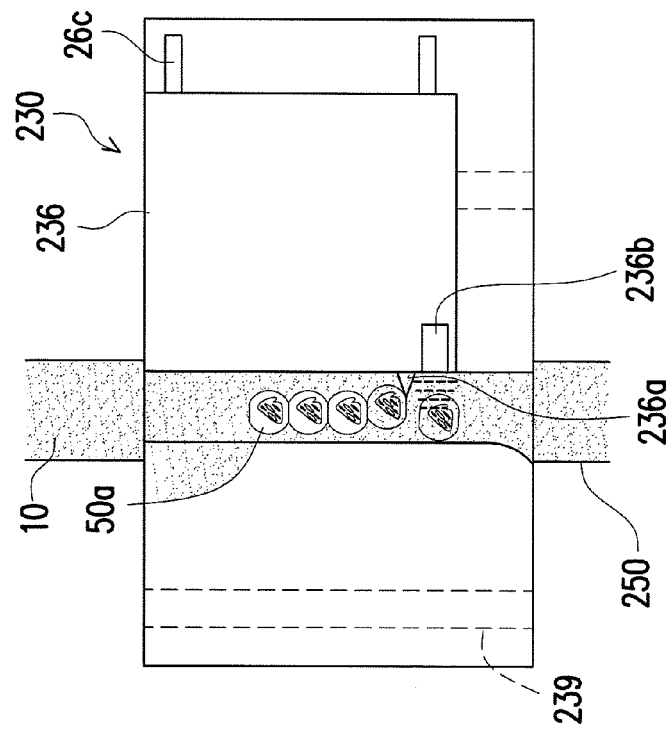
Figure 6F:
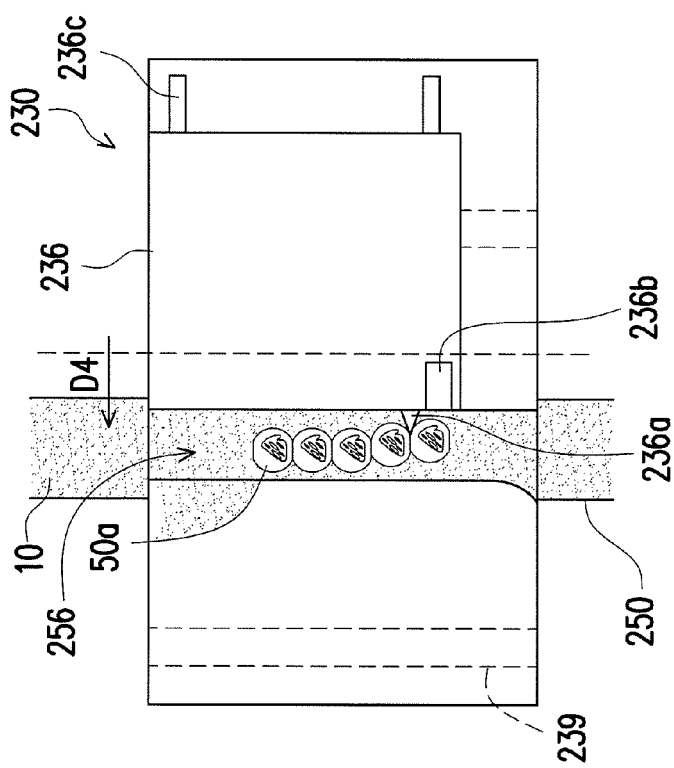

Next, as shown in FIG. 6E and FIG. 6F, the separation device 236 can slide along a fourth direction D4 indicated by an arrow shown in FIG. 6E, namely, towards a direction of the sequencing area 256 of the flow channel 250, and the contact portion 236a of the separation device 236 can approach or contact an intersection at where the sample slices 50a lap over or contact with each other. Moreover, the piezoelectric device 236b can be triggered into vibration and thereby drive the separation device 236 into vibration. Therefore, the contact portion 236a can separate the sample slices 50a that are in contact with or lapped over each other via the vibration of the separation device 236 (in FIG. 6F, dashed lines at a side of the piezoelectric device 236b are used to represent a vibration direction of the separation device 236).

Figure 6H:
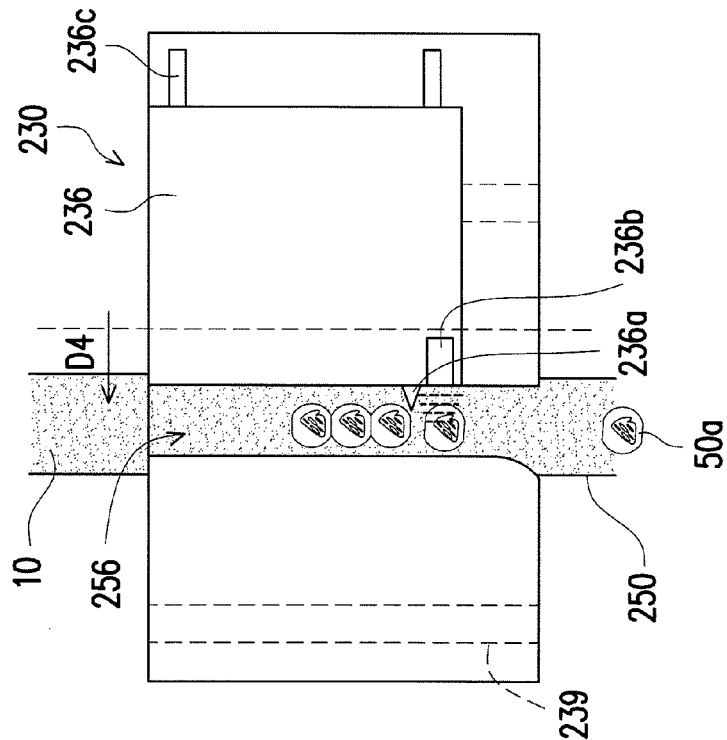
Figure 6G:
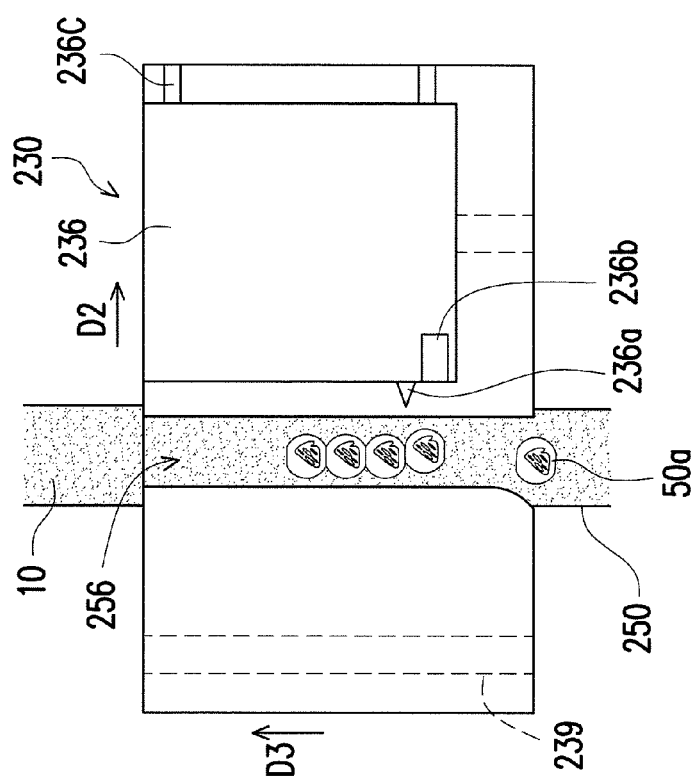

As shown in FIG. 6G and FIG. 6H, when the sample slices 50a located at the front end of the sample chain are separated, the separation device 236 can move out away from the sequencing area 256 of the flow channel 250 along a second direction D2, and the sequencing module 230 can slide relative to the flow channel 250 and move along a third direction D3 indicated by an arrow shown in the left side of FIG. 6G so as to enable the separation device 236 to move towards a connecting region with the next adjacent or overlapping sample slice 50a.

Next, as shown in FIG. 6H, when the separation device 236 slides along the extending direction of the flow channel 250 and approaches to the connecting region with another adjacent or overlapping sample slice 50a, the separation device 236 can further slide relative to the first body 232 along the slide rail 236c towards the direction of the sequencing area 256 of the flow channel 250, namely, move towards a fourth direction D4 as indicated by an arrow shown in FIG. 6H, so that the contact area 236a of the separation device 236 can approach or contact a connecting region with the next sample slice 50a. Next, the piezoelectric device 236b can be triggered again to drive the separation device 236 into vibration so as to separate out the next sample slice 50a.

In the present embodiment, the sequencing module 230 can continuously repeat perform the aforementioned steps until all the sample slices 50a in the sample chain are sequentially separated and enter into the sequencing area 256 of the flow channel 250.

Figures 7A, 7B:
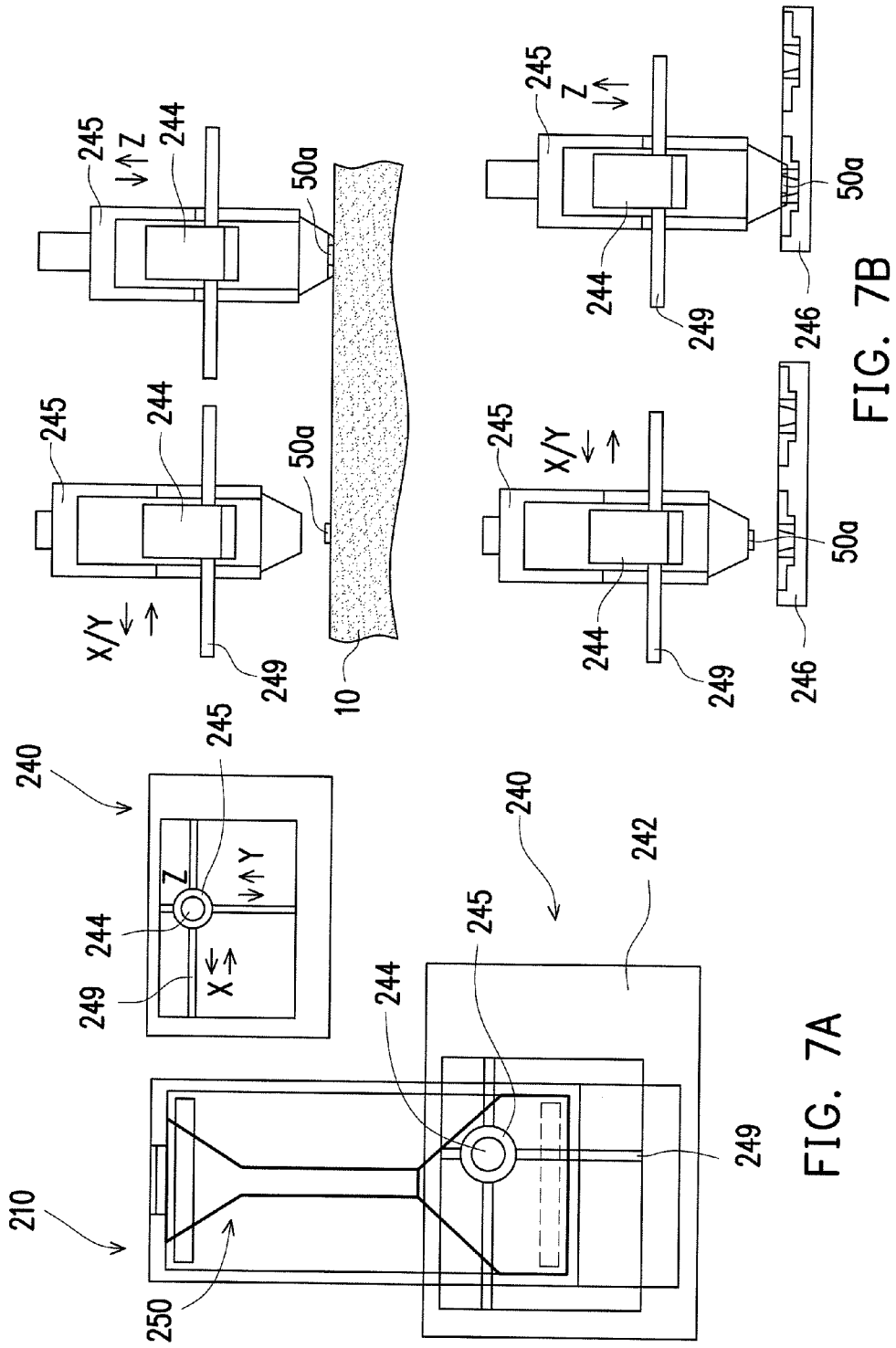
FIG. 7A to FIG. 7C are schematic views illustrating a pickup module in the sample preparation system of FIG. 2.
Figure 7C:
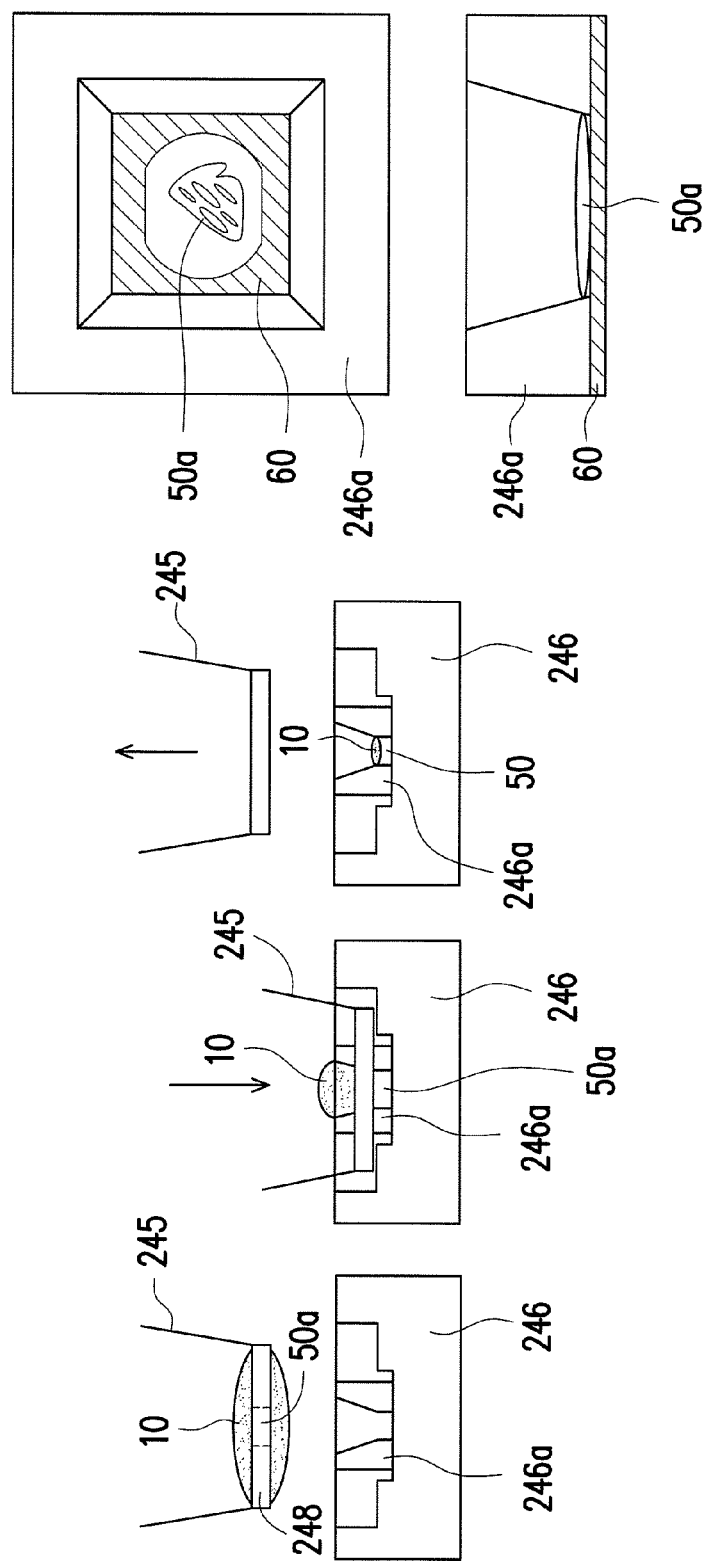

FIG. 7A to FIG. 7C are schematic views illustrating the pickup module in the sample preparation system of FIG. 2. In the present embodiment, the pickup module 240 may include a second body 242, a pickup device 245 and a second detection device 244. The pickup device 245 is, for example, mounted on the second body 242, and the second detection device 244 can be disposed corresponding to the first tank 210 so as to detect the positions of the sample slices 50a. In the present embodiment, the pickup device 245 can move relative to the first tank 210 according to a detection result of the second positioning unit 244.

In detail, the pickup device 245 can be mounted on the second body 241 through the slide rail 249, and as shown in FIG. 7A, the pickup device 245 can move in the XY plane directions. In addition, the pickup device 245 can also move vertically upwards and downwards along the sliding shaft 247 in the Z direction. In other words, in the present embodiment, the pickup device 245 can be actuated in three-dimensional directions. Furthermore, in the present embodiment, the second detection device 244 is embedded in the pickup device 245 and slidably disposed on the slide rail 249 so as to move in the XY plane directions and to detect the positions of the sample slices 50a.

As shown in top diagrams of FIG. 7B, the second detection device 244 can move along the slide rail 249 in the XY plane directions and detect the sample slices 50a floated on the fluid surface of the fluid 10 in the first tank 210 via an opening at the bottom of the pickup device 245. In addition, after the second detection device 244 detects the sample slices 50a, the pickup device 245 can move vertically along the sliding shaft 247 in the Z direction, so that the pickup device 245 can move towards the direction of the fluid surface of the fluid 10 to pick up the sample slices 50a from the first tank 210.

Next, as shown in bottom diagrams of FIG. 7B, the pickup device 245 can further move vertically upwards along the sliding shaft 247, then along the XY plane directions, and move above the sample holders 246 according to a detection result of the second detection device 244. Nevertheless, the pickup device 245 can move vertically downwards along the Z direction, and thus can unload the sample slices 50a onto the sample holders 246.

Referring to FIG. 7C, in the present embodiment, the pickup device 245 has a pickup ring 248 disposed at the bottom thereof. When picking up the sample slices 50a in the first tank 210 with the pickup device 245, the pickup ring 248 can contact with the fluid surface of the fluid 10 so as to form the pickup ring 245 in the liquid membrane. In the present embodiment, a thickness of the sample slices 50a is, for example, smaller than 70 nm, and a maximum width of the sample slices 50a is, for example, smaller than 1.2 mm. Because each of the sample slices 50a is very thin, a surface tension of the liquid membrane is sufficient to bear the sample slices 50a, and the sample slices 50a can be attached onto the liquid membrane so as to take out the sample slices 50a from the first tank 210 sequentially.

Next, as shown in FIG. 7C, the pickup device 245, after picking up the sample slice 50a, can move above the sample holder 246. In the present embodiment, sample holder 246 has a silicon base 246a disposed thereon for accommodating the sample slice 50a. Moreover, the pickup device 245 can move downwards along an arrow direction so as to unload the sample slice 50a on the silicon base 246a of the sample holder 246. In the present embodiment, the silicon base 246a can have an opening 246a1, and the opening 246a1 is disposed with a silicon nitride film 60 therein for accommodating the sample slice 50a.

After the sample slice 50a is accommodated in the opening 246a1 of the silicon base 246a, the pickup device 245 can move vertically upwards to leave the sample holder 246. In the present embodiment, by using the liquid membrane formed in the pickup ring 248 to carry the sample slice 50a, a surface of the sample slice 50a can be prevented from being rubbed by the pickup device 245. Moreover, the present embodiment encapsulates the sample slice 50a with the liquid membrane so as to reduce a chance for the surface of the sample slice 50a to contact with air when being picked up and transferred by the pickup device 245, thereby providing a better protection to the sample slice 50a, and thus various properties of the sample can be avoided from being damaged.

Figure 8:
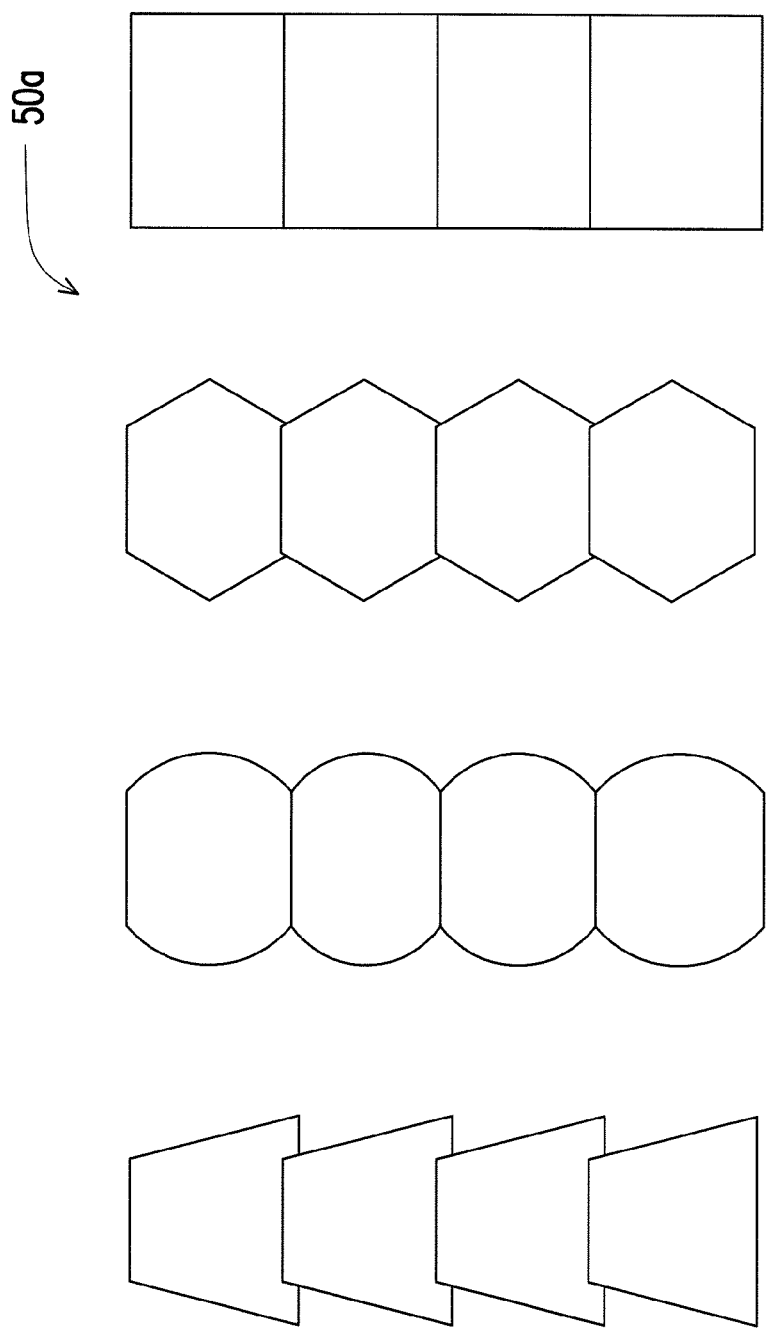
FIG. 8 is schematic view illustrating a plurality of sample slices in the sample preparation system of FIG. 2.

FIG. 8 is schematic view illustrating the sample slices in the sample preparation system of FIG. 2. As described in the above, in the present embodiment, the sample block 50, after being sequentially sliced by the slicing module 110, can form a plurality of sample slices 50a having the same profile or a continuous trend of profile variation. In the present embodiment, profiles of the sample slices 50a are corresponded to different appearances of the sample block 50. For instance, since cross-sections of different sample blocks 50 can be different shaped, the sample slices 50a sliced by the slicing module 110 can also have a variety of different profiles. As shown in FIG. 8, in the present embodiment, the profiles of the sample slices 50a can be trapezoids, double truncated circles, polygons, squares or so forth. In addition, the profile design of the sample block 50 enables the sample slices 50a to lapped over each other to form the sample chain when the sample block 50 are sequentially sliced into the sample slices 50a.

In the present embodiment, since different batches of the sample slices 50a aimed by different sample blocks 50 have different profiles, the profiles of the sample slices 50a can be used as identification marks for different batches of the sample slices 50a. Moreover, in a same sample block 50a, sample slices 50a with gradually increasing or gradually decreasing profile sizes can also be formed due to cross-sectional widths of the sample block 50a being gradually increasing or gradually decreasing. In the present embodiment, a trend of the profile variation of the same batch of the sample slices 50a can be used as an indication and a basis for determining an order for the sample slices 50a to be observed under the electron microscope.

Figure 9:
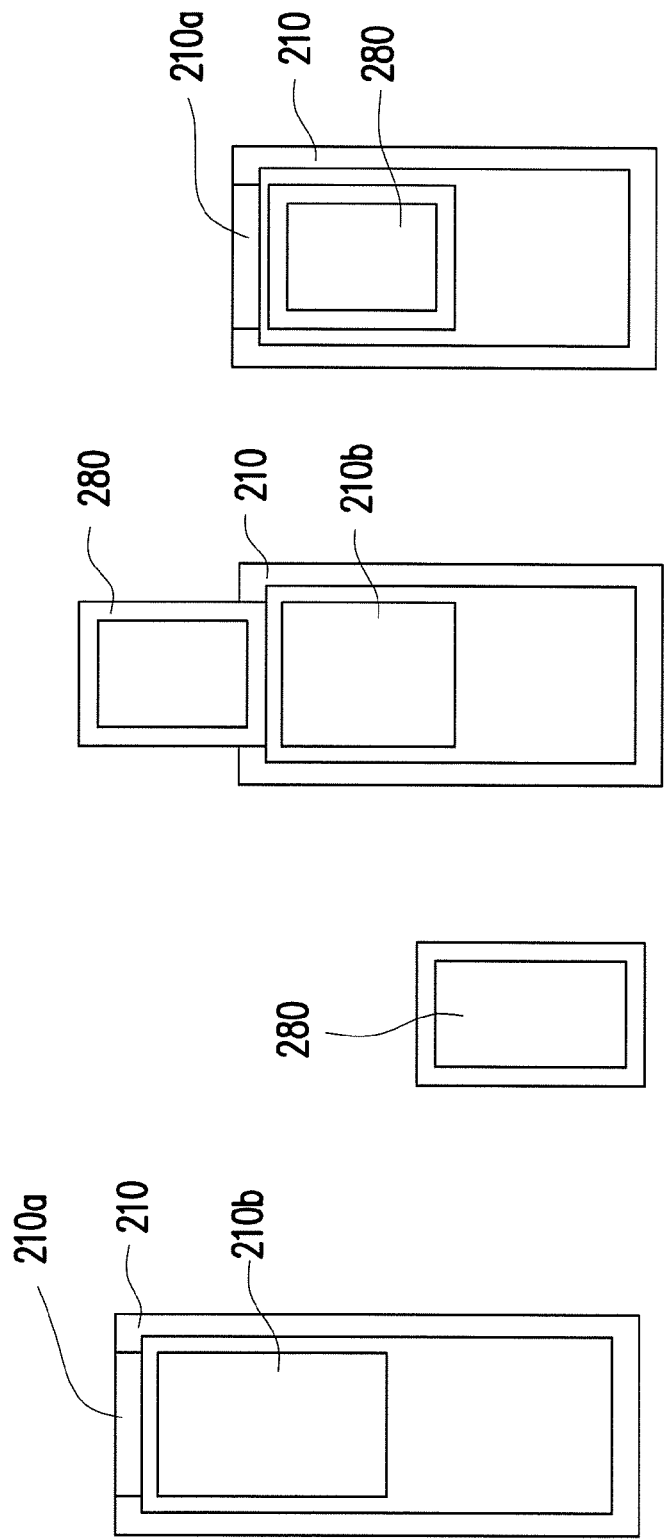
FIG. 9 and FIG. 10 are schematic views illustrating a sample preparation system according to another embodiment of the present disclosure.
Figure 10:
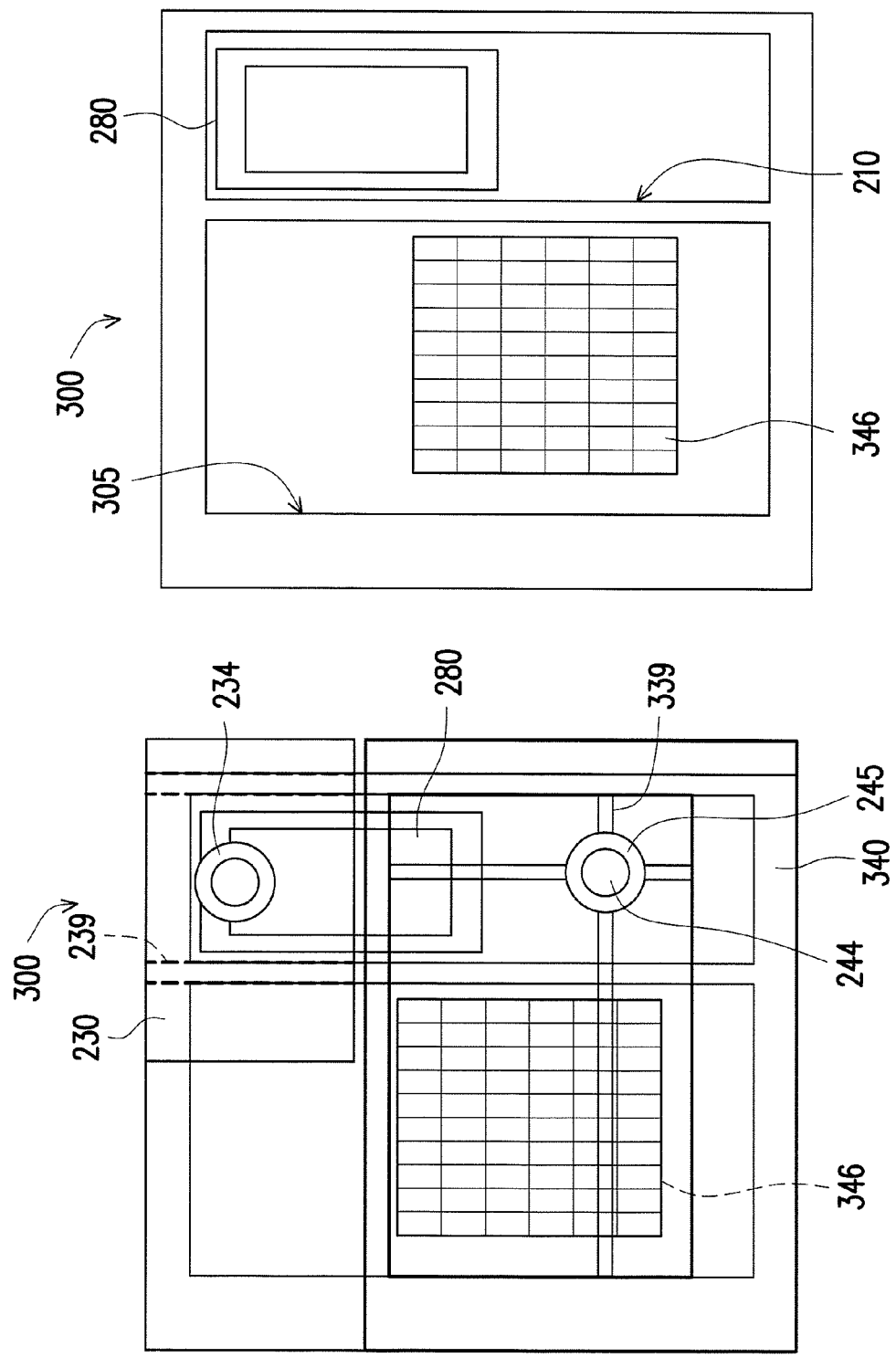

FIG. 9 and FIG. 10 are schematic views illustrating a sample preparation system 300 according to another embodiment of the present disclosure. Referring to FIG. 9 and FIG. 10, the present embodiment is similar to the previous embodiment of FIG. 2; and thus, the same or similar notations are used for representing the same or similar components, and descriptions of the same technical contents are omitted. Differences between the present embodiment and the previous embodiment lie in that: the first tank 210 of the sample preparation system 300 may further has a first embedding groove 210a and a second embedding groove 210b, and the second tank 280 can be embedded at a side of the first tank 210 or in the first tank 210 through the first embedding groove 210a or the second embedding groove 210b.

As shown in FIG. 9, in the present embodiment, the second tank 280 can receive the sliced sample slices 50a from the slicing module 110 shown in FIG. 2, and then, with the flowing of the fluid 10 injected into the second tank 280, the sample slices 50a can be moved into the first tank 210 from the second tank 280. For instance, when the second tank 280 is embedded at a side of the first tank 210, the sample slices 50a can be transferred from the second tank 280 into the first tank 210 by disposing the second tank 280 in a tilted manner or stirring the fluid 10 in the second tank 280, so as to perform the subsequent sequencing and picking up-and-placing processes of the sample slices 50a.

In the present embodiment, the second tank 280 is embedded in the first tank 210 so that the first tank 210, through the configuration of the second tank 280, can collaborate with various types of slicing module 110 so as to receive the sample slices 50a sliced by the various types of slicing module 110.

Moreover, referring to FIG. 10, in the present embodiment, the sample preparation system 300 includes the second tank 280 which is embedded in the first tank 210. In addition, the sample preparation system 300 has an open slot 305 and a sample holder arrangement area 346 accommodated in the open slot 305. In the present embodiment, after the second tank 280 receives the sample slices 50a from the slicing module 110, the second tank 280 can be embedded in the first tank 210. Next, the fluid 10 can be slowly injected into the first tank 210, and when the fluid surface of the first tank 210 in the fluid 10 is higher than the second tank 280, the entire second tank 280 is immersed in the fluid 10. At this moment, the sample slices 50a in the second tank 280 can be transferred to the fluid surface of the fluid 10 in the first tank 210 along with the rising of the fluid surface of the fluid 10.

The sequencing module 230 and the pickup module 340 are respectively disposed on the first tank 210 to sequentially separate the sample slices 50a on the fluid surface of the first tank 210. Next, the pickup module 340 can transfer the separated sample slices 50a sequentially on to the holder arrangement area 346.

The sample preparation system 300 and the first tank 210 of the present embodiment, with the design and configuration of the second tank 280, can divide the sequencing and the picking up-and-placing of the sample slices and the sample into two independent steps so that the first tank 210 of different design or size can be applied to various different types of slicing module made by different manufacturers. Thus, the process line of the sample slices 50a can be more flexible in terms of planning, and the operation or the maintenance of the overall sample preparation system 300 can be more convenient.

Figure 11:
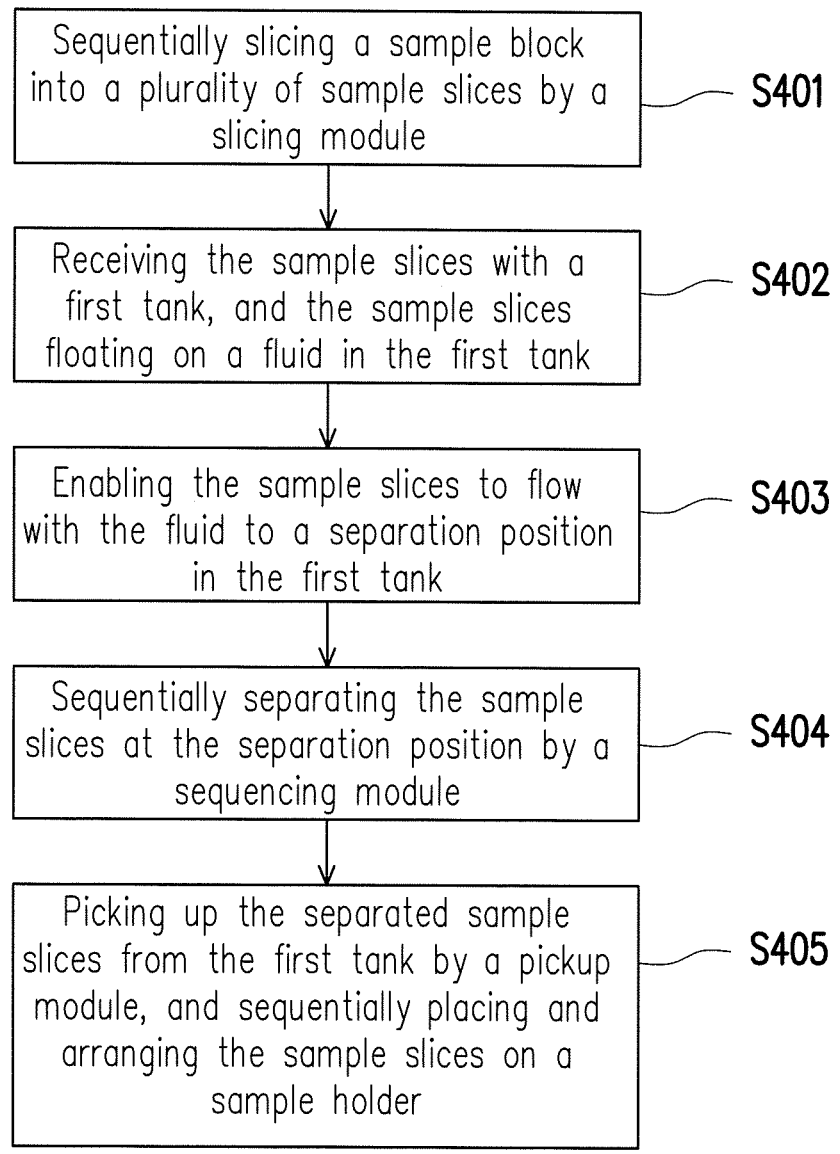
FIG. 11 is a schematic flow chart illustrating a sample preparation method according to an embodiment of the present disclosure.

FIG. 11 is a schematic flow chart illustrating a sample preparation method according to an embodiment of the present disclosure. Referring to FIG. 2, FIG. 3A to FIG. 3C and FIG. 11, preparation steps of the sample slices 50a includes: sequentially slicing the sample block 50 in to the sample slices 50a by slicing module 110 (step S401). In the present embodiment, since the sample slices 50a in a same batch are formed by sequentially slicing a same piece of sample block 50, the sample slices 50a may have the same profile or profiles respectively corresponding to cross-sections at different portions of an extending axial direction of the sample block 50.

Next, the sample slices 50a are received by the first tank 210, and the sample slices 50a float on the fluid 10 in the first tank 210 (step S402). Then, the sample slices 50a as carried by the flow of the fluid 10 are moved to a separation position in the first tank 210 (step S403). In the present embodiment, the separation position of the sample slices 50a is, for example, located at the sequencing area 256 in the flow channel 250 shown in FIG. 3A. Next, the sample slices 50a, as located in the separation position in the sequencing area 256, are sequentially separated by the sequencing module 230 (step S404). Afterwards, the pickup module 240 picks up the separated sample slices 50 from the first tank 210, and the pickup module 240 sequentially places the sample slices 50a onto the sample holders 246 (step S405). At this point, all the processing steps of slicing the sample block 50 and the sequencing and arranging of the sample slices 50a are substantially completed.

In summary, the sample preparation system and the sample preparation method in the embodiments of the present disclosure can sequentially slice the sample block with the slicing module so as to form a plurality of sample slices in a same batch. Different batches of the sample slices formed by slicing different sample blocks may have different profiles to serve as the identification marks for the different batches of the sample slices. In addition, the sample slices in the same batch can also have different profile sizes or shapes according to a variation in appearance profile of the sample block, and a trend of profile variation of the sample slices formed by sequentially slicing is corresponded to the variation in appearance profile of the sample block. The different profile sizes or shapes of the sample slices in the same batch can be used as the indication and the basis for determining the order for the sample slices to be observed under the electron microscope.

In the embodiments of the present disclosure, the sample slices sliced by the slicing module can be received by the tank, and the sample slices can float on the fluid in the tank. The fluid in the tank can carry the sample slices to flow along the flow channel disposed in the tank. In addition, the sequencing module and the pickup module are respectfully disposed on the flow channel. The sequencing module can separate the sample slices that are in contact with or lapped over each other, and the pickup module can sequentially transfer the separated sample slices from the tank onto the sample holders and sequentially arrange the samples slices on the sample holders. The sample preparation system and the sample preparation method of the embodiments of the present disclosure can achieve a sequential preparation of a large number of thin sample slices in an automated manner, and thereby greatly reduce the preparation time of the sample slices, lower the sample damage and the manpower during the processing, and fulfil the correct sequencing and arrangement of a large number of samples.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A sample preparation system, comprising:
    a slicer, sequentially slicing a sample block into a plurality of sample slices;
    a first tank, configured to receive the sample slices, wherein the sample slices float on a fluid in the first tank and be moved as the fluid flows;
    a sample separator, disposed at a side of the first tank so as to separate the sample slices sequentially; and
    a sample mover, coupled to the first tank so as to pick up the sample slices sequentially from the first tank and place the sample slices on corresponding sample holders.

2. The sample preparation system as recited in claim 1, wherein the slicer comprises:
    a clamping portion, configured to clamp the sample block; and
    a cutting tool, disposed at an edge of the first tank so as to sequentially slice the sample block.

3. The sample preparation system as recited in claim 1, wherein the first tank further comprises:
    a tank body, having a chamber and a liquid inlet and a liquid outlet connected through with the chamber, the fluid entering the chamber via the liquid inlet and leaving the chamber from the liquid outlet by flowing along a flow channel, wherein the flow channel comprises:
        a receiving area, adjacent to the liquid inlet and configured to receive the sample slices;
        a pickup area, adjacent to the liquid outlet, wherein the sample mover picks up the sample slices from the pickup area; and
        a sequencing area, located between the receiving area and the pickup area, wherein the sample slices sequentially pass through the sequencing area, and the sample separator separate the sample slices.

4. The sample preparation system as recited in claim 3, wherein a width of the sequencing area is smaller than widths of the receiving area and the pickup area.

5. The sample preparation system as recited in claim 3, wherein the sample separator is disposed on the flow channel, and the sample separator comprises:
    a first body;
    a first detection device, disposed corresponding to the flow channel so as to determine positions of the sample slices; and a separation device, disposed on the first body and moving towards the sample slices in the first tank so as to separate two adjacent sample slices.

6. The sample preparation system as recited in claim 5, wherein the sample separator further comprises a piezoelectric device coupled to the separation device to drive the separation device into vibration so as to separate the two adjacent sample slices.

7. The sample preparation system as recited in claim 5, wherein the first body of the sample separator is slidably disposed on the first tank along a first direction.

8. The sample preparation system as recited in claim 7, wherein the separation device of the sample separator is slidably disposed on the first body along a second direction, and the first direction and the second direction are orthogonally intersected.

9. The sample preparation system as recited in claim 1, wherein the sample mover comprises:
a second body;
a pickup device, disposed on the second body; and
a second detection device, disposed corresponding to the first tank so as to detect positions of the sample slices, wherein the pickup device moves with respect to the first tank according to a detection result of the second positioning unit, so as to pick up the sample slices sequentially from a pickup area and to place the sample slices on the corresponding sample holders.

10. The sample preparation system as recited in claim 1, further comprising a second tank coupled to a side of the first tank or disposed in the first tank, wherein the second tank receives the sample slices from the slicer, and the sample slices are carried by the fluid to move from the second tank to the first tank.

11. The sample preparation system as recited in claim 1, wherein profile shapes of the sample slices comprise trapezoids, double truncated circles or polygons.

12. A sample preparation method, comprising:
sequentially slicing a sample block into a plurality of sample slices by a slicer;
receiving the sample slices with a first tank, wherein the sample slices float on a fluid in the first tank;
enabling the sample slices to flow with the fluid to a separation position in the first tank;
sequentially separating the sample slices at the separation position by a sample separator; and
picking up the separated sample slices from the first tank by a sample mover, and sequentially placing and arranging the sample slices on a sample holder.

13. The sample preparation method as recited in claim 12, further comprising:
when the slicer sequentially slices the sample block, with a profile shape design of the sample block, enabling the sequentially sliced sample slices received by the first tank to lap over each other to form a sample chain floating on the fluid in the first tank.

14. The sample preparation method as recited in claim 13, wherein the sample separator has a separation device configured to approach or contact the sample chain and to separate each of the sample slices.

15. The sample preparation method as recited in claim 12, further comprising:
after the slicer sequentially slices the sample block into the sample slices, receiving the sample slices from the slicer with a second tank.

16. The sample preparation method as recited in claim 15, further comprising:
transferring the sample slices from the second tank to the first tank, wherein the second tank is movably embedded at a side of the first tank or disposed in the first tank, and the fluid is injected into the second tank to carry the sample slices from the second tank to the first tank with the fluid, so as to sequentially perform subsequent separation steps of the sample slices.

* * * * *